United States Patent [19]

Guittard et al.

[11] Patent Number: 4,576,604
[45] Date of Patent: Mar. 18, 1986

[54] OSMOTIC SYSTEM WITH INSTANT DRUG AVAILABILITY

[75] Inventors: George V. Guittard, Cupertino; Joseph C. Deters, Mountain View; Felix Theeuwes, Los Altos; Richard Cortese, San Jose, all of Calif.

[73] Assignee: ALZA Corporation, Palo Alto, Calif.

[21] Appl. No.: 472,333

[22] Filed: Mar. 4, 1983

[51] Int. Cl.[4] .......................... A61K 9/22; A61K 9/00
[52] U.S. Cl. ..................... 604/890; 604/891; 604/896
[58] Field of Search ............................. 604/890–896; 424/14, 16, 21, 28

[56] References Cited

U.S. PATENT DOCUMENTS

| | | | |
|---|---|---|---|
| 2,099,402 | 11/1937 | Keller | 424/21 |
| 2,921,001 | 1/1960 | McDermott | 424/16 |
| 3,577,512 | 5/1971 | Shepherd et al. | 424/21 |
| 3,625,214 | 12/1971 | Higuchi | 424/21 |
| 4,116,241 | 9/1978 | Theeuwes et al. | 424/21 |
| 4,122,157 | 10/1978 | Huber | 424/21 |
| 4,138,344 | 2/1979 | Choi et al. | 604/894 |
| 4,142,526 | 3/1979 | Zaffaroni et al. | 604/894 |
| 4,454,108 | 8/1982 | Iida et al. | 424/14 |
| 4,455,143 | 3/1982 | Theeuwes et al. | 604/890 |

Primary Examiner—C. Fred Rosenbaum
Assistant Examiner—Sherri E. Vinyard
Attorney, Agent, or Firm—Paul L. Sabatine; Edward L. Mandell; Steven F. Stone

[57] ABSTRACT

An osmotic device is disclosed for delivering a beneficial agent. The device comprises a wall surrounding a compartment containing an agent, a passageway in the wall connecting the exterior of the device with the compartment, and (a) an agent in the wall or (b) an agent carried on the wall in the wall. The device delivers the agent from the compartment and the wall.

34 Claims, 21 Drawing Figures 4,576,604

OSMOTIC SYSTEM WITH INSTANT DRUG AVAILABILITY

FIELD OF THE INVENTION

This invention pertains to a therapeutic system that is a controlled dosage form. The therapeutic osmotic system provides a preprogrammed, unattended delivery of a beneficial drug, that is initially delivered in an increased therapeutically effective amount, followed by delivery of drug at a controlled rate, and for a time period, established to meet a specific therapeutic need. The osmotic system is manufactured in the form of an osmotic device for delivering drug to a selected drug receptor site.

BACKGROUND OF THE INVENTION

Osmotic therapeutic systems manufactured in the form of osmotic devices for the precision administration of drugs with control of delivery patterns, and with extended operational delivery times are known in U.S. Pat. Nos. 3,845,770 and 3,916,899 both issued to inventors Felix Theeuwes and Takeru Higuchi. The osmotic systems disclosed in these pioneer patents are made of a semipermeable wall that surrounds a reservoir containing drug. The wall is permeable to the passage of an external fluid, impermeable to the passage of drug, and it has a passageway through the semipermeable wall for delivering drug from the osmotic system. These systems are extraordinarily effective for delivering a drug that is soluble in the fluid, and also for delivering a drug that has limited solubility in the fluid and is mixed with an osmotically effective compound that is soluble in the fluid and exhibits an osmotic pressure gradient across the wall against the fluid. The osmotic systems release drug by fluid being imbibed through the semipermeable wall into the reservoir at a rate determined by the permeability of the semipermeable wall and the osmotic pressure gradient across the wall producing a solution of soluble drug, or a solution of soluble compound containing drug, which solution in either operation is delivered at a controlled rate over a prolonged period of time.

An unobvious and unexpected advance was made in osmotic systems by patentees Felix Theeuwes and Atul D. Ayer as disclosed in U.S. Pat. Nos. 4,008,719; 4,014,334; 4,058,122; 4,116,241; 4,160,452; and 4,256,108. In these patents, the patentees provided osmotic systems comprising a laminated wall formed of two laminae, a semipermeable lamina and a microporous lamina, that act in cooperation to provide improved controlled delivery of drug over a prolonged period of time. The two laminae maintain their physical and chemical integrity during the controlled dispensing of drug, and the laminate allows a wider control over the rate at which drug is delivered to a drug receptor site over a prolonged period of time.

While the above osmotic systems comprising a single layer semipermeable wall, and the osmotic systems comprising the laminated wall consisting of a semipermeable lamina and a microporous lamina represent outstanding and pioneering advancements in the osmotic delivery art, and while they are useful for dispensing innumerable drugs to the environment of use, it has now been discovered that these osmotic systems can be improved further to enhance the drug delivery kinetics and the usefulness of the osmotic systems. That is, it has now been discovered unexpectedly that osmotic systems can be provided that initially deliver a bio-affecting drug in an increased amount followed by a substantially constant amount at a controlled rate over time; thereby, making drug available instantly to a drug receptor by substantially eliminating the start-up drug delivery time frequently required to deliver some drugs by osmotic systems. The therapeutic osmotic systems made available by this invention embodying the unique initial drug delivery followed by controlled and constant prolonged delivery, thereby function according to a pre-selected built-in optimal program of drug presentation.

OBJECTS OF THE INVENTION

Accordingly, in view of the above presentation, it is an immediate object of this invention to provide an improved osmotic delivery system for the controlled delivery of drug initially in an increased amount followed by a constant amount to a drug receptor site over a prolonged period of time.

Another object of the invention is to provide an osmotic system comprising a semipermeable wall containing drug that is available for instant delivery in an increased amount thereby providing an osmotic system that delivers drug immediately when in operation in the environment of use.

Another object of the invention is to provide an osmotic system comprising a laminated wall comprising an interior lamina and an exterior lamina, which latter lamina contains a drug that is available for immediate delivery as a burst of drug for substantially eliminating the start-up time sometimes required for certain drugs.

Another object of the invention is to provide an osmotic system manufactured in the form of an osmotic device that comprises an outermost lamina consisting essentially of a composition of drug and a releasable binder that delivers drug immediately for increasing the period of time drug is available for performing its beneficial effects.

Yet still another object of the invention is to provide an osmotic system adapted for administering drug to an animal from a drug-containing outermost lamina for delivering an initial drug-pulse which acts in cooperation with the osmotic system that follows with drug delivery at a rate controlled by the osmotic system.

Still yet another object of the invention is to provide a method for forming a microporous lamina in a biological environment for increasing the volume of fluid available for imbibition by an osmotic device, while concomitantly increasing the amount of drug available to the biological environment.

Still yet another object of the invention is to provide a method for increasing the amount of drug available for producing a beneficial effect by making available an osmotic device that delivers an increased amount of drug for diminishing the incidence of drug loss attributed to the unwanted metabolic effects of the gastrointestinal tract or the unwanted metabolic effects of drug passage through the liver.

Yet still another object of the invention is to provide (1) a laminate comprising a semipermeable lamina in laminar arrangement with a lamina formed of a water-soluble material containing drug; (2) a laminate comprising a semipermeable lamina containing drug in laminar arrangement with a lamina formed of a water-soluble material containing drug; (3) a laminate comprising a semipermeable lamina in laminar arrangement with a microporous lamina which latter lamina is in laminar arrangement with a lamina formed of a water-soluble polymer containing drug; and (4) a laminate comprising a semipermeable lamina in laminar arrangement with a microporous lamina containing drug, which microporous lamina is in laminar arrangement with a lamina formed of a water-soluble material containing drug, and wherein laminates 1 through 4 are useful for manufacturing osmotic systems.

Other objects, features and advantages of the invention will be more apparent to those skilled in the art from the following detailed specification, taken in conjunction with the drawings and the accompanying claims.

BRIEF DESCRIPTION OF THE DRAWINGS

In the drawings, which are not drawn to scale, but are set forth to illustrate various embodiments of the invention, the figures are as follows.

In the drawings and the specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWINGS

Figure 1:
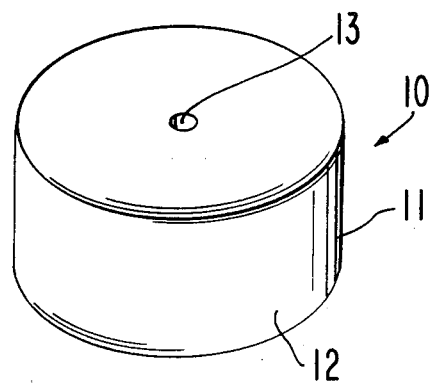
FIG. 1 is an isometric view of an osmotic device designed for orally administering a beneficial agent to the gastrointestinal environment.

Turning now to the drawings in detail, which are examples of various osmotic systems provided by the invention, and which examples are not to be construed as limiting, one embodiment of an osmotic system is seen in FIG. 1 as indicated by the numeral 10. In FIG. 1, osmotic system 10 is manufactured as an oral, osmotic device comprising a body 11 that can be shaped, sized, adapted and structured for easy placement and prolonged retention in a biological environment of use for the controlled delivery of a beneficial agent thereto. Osmotic device 10 comprises wall 12 with a passageway 13 through wall 12 for connecting the inside of osmotic device 10 with the exterior of osmotic device 10.

Figure 2:
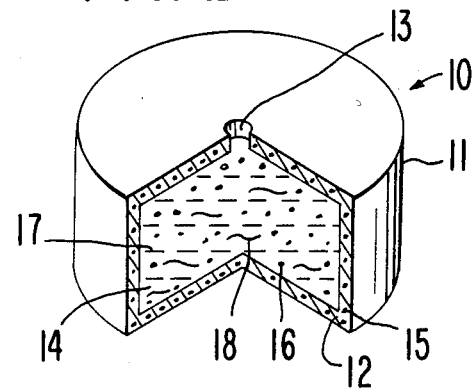
FIG. 2 is an opened view of the osmotic device of FIG. 1 with FIG. 2 illustrating the structure of the osmotic device.

In FIG. 2, osmotic device 10 is seen in opened-section. In FIG. 2, device 10 comprises body 11 having wall 12 that surrounds and forms a compartment 14. Wall 12 is formed of a semipermeable polymer that is permeable to the passage of an exterior fluid and substantially impermeable to the passage of drugs and osmotically effective agents. Wall 12 contains a drug 15, represented by dots, that is released instantly, or in a short time, from wall 12 when device 10 is in operation in a biological environment of use. Wall 12 of device 10 is substantially inert, it maintains its physical and chemical integrity during the dispensing of an active beneficial drug, and it is formed of a semipermeable material that is nontoxic to a host. A passageway 13 in wall 12 connects compartment 14 with the exterior of device 10. Compartment 14 houses beneficial drug 16 that is soluble in an external fluid 17, represented by dashes, imbibed through semipermeable wall 12 into compartment 14, and it exhibits an osmotic pressure gradient across wall 12 against an external fluid. Compartment 14 optionally contains an osmotically effective solute 18, represented by wavy lines, that is soluble in the fluid and exhibits an osmotic pressure gradient across wall 12.

In operation, osmotic device 10 of FIGS. 1 and 2, manufactured in the form of an osmotic tablet, on entering a biological fluid environment of use, such as the gastrointestinal tract of a warm-blooded animal, initially delivers drug 15 from wall 12 to the environment of use. This initial delivery of drug 15 makes drug available immediately to the host by eliminating the start-up time needed before drug is delivered by device 10. The delivery of drug 15, usually over a period of an hour or more, is effected independent of delivery of drug 16 by device 10. Device 10 may deliver drug 16 during the period of time drug 15 is delivered, or device 10 may deliver drug 16 after delivering of drug 15. Drug 15 and drug 16 may in an optional embodiment be the same drug or different drug.

Osmotic device 10 releases drug 16 contained in reservoir 14 by fluid being imbibed into compartment 14 in a tendency towards osmotic equilibrium at a rate controlled by the permeability of semipermeable wall 12 and the osmotic pressure gradient across semipermeable wall 12 to continuously dissolve agent 16, which is osmotically pumped from compartment 14 through passageway 13 at a controlled and continuous rate over a prolonged period of time. Osmotic device 10, also releases agent 16 that has limited solubility in fluid 17 and is mixed with an osmotically effective compound 18 by fluid 17 being imbibed through semipermeable wall 12 into reservoir compartment 14, in a tendency towards osmotic equilibrium at a rate controlled by the permeability of wall 12 and the osmotic pressure gradient across wall 12, to continuously dissolve osmotically effective compound 18 and form a solution thereof containing drug 16 that is released from device 10 through passageway 13 at a controlled and continuous rate over a prolonged period of time.

Figure 3:
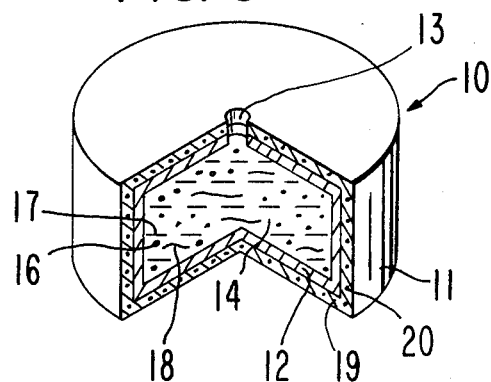
FIG. 3 is an opened view of the osmotic device depicting the semipermeable wall of the device bearing an exterior fluid-soluble lamina containing drug.

FIG. 3 represents another therapeutic osmotic device manufactured according to the invention for administering drug to a drug receptor. In the illustrated embodiment, osmotic device 10 is seen with a section removed and it comprises body 11, semipermeable wall 12, passageway 13, and compartment 14 containing drug 16, imbibed fluid 17 and osmotically effective compound 18. Device 10 of FIG. 3 comprises further a lamina 19 coated onto the exterior surface of semipermeable wall 12. Lamina 19 is formed of an aqueous soluble material, an aqueous disintegrating material, or the like, and it contains drug 20. Lamina 19 containing drug 20 is provided for making available instantly drug 20. In operation when device 10 is in a fluid environment, lamina 19 dissolves or undergoes dissolution and concurrently delivers drug 20 to a drug receptor. Lamina 19 containing drug 20 by providing immediate drug delivery, overcomes the time required for drug 16 to be delivered from device 10. A start-up time is needed frequently for imbibing fluid through semipermeable wall 12, and for hydrating with imbibed fluid 17 a drug that lost its water of hydration during drying or solvent evaporation processes used for manufacturing device 10. Lamina 19 containing drug 20 operates independent of device 10 which device 10 delivers drug 16 as described for FIG. 2. While FIG. 3 depicts lamina 19 containing drug 20, and FIG. 2 depicts semipermeable wall 12 containing drug 15, it is understood the invention embraces an osmotic device 10 comprising a semipermeable wall 12 containing drug 15 laminated with lamina 19 containing drug 20.

Figure 4:
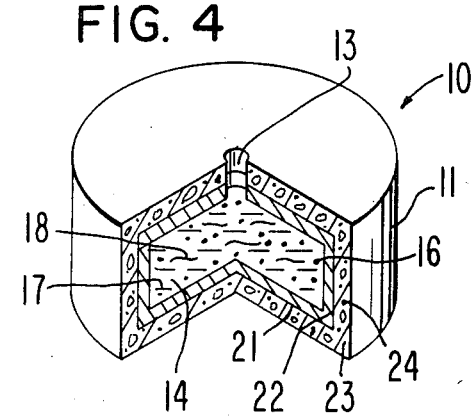
FIG. 4 is an osmotic device with a section removed for depicting the internal structure and the laminated wall comprising an outer lamina housing releasable drug.

FIG. 4 illustrates in opened view an osmotic system 10 made in the form of an oral, osmotic device comprising body 11 and a laminated wall 21 that surrounds reservoir compartment 14. Laminated wall 21 has a portal or passageway 13 that communicates with compartment 14 and the exterior of osmotic device 10. Compartment 14 contains beneficial drug 16 that is soluble in external fluid 17 imbibed through laminated wall 21, and drug 16 exhibits an osmotic pressure gradient across laminated wall 12 against an external fluid. Optionally, compartment 14 contains drug 16 having limited solubility in the fluid and it is present in compartment 14 with an osmotically effective solute 18. Solute 18 is soluble in the fluid and it exhibits an osmotic pressure gradient across laminated wall 12.

Laminated wall 21 comprises a semipermeable lamina 22 that is the interior lamina facing compartment 14, and a microporous lamina 23, distant from compartment 14 and in the osmotic device of FIG. 4, microporous lamina 23 is the exterior lamina facing the environment of use. Semipermeable lamina 22 is permeable to the passage of an external fluid and it is substantially impermeable to the passage of drug and other agents. Semipermeable lamina 22 is formed of a material that maintains its physical and chemical integrity in the presence of drug, agent and fluid, it is substantially non-erodible and inert, and it can be made from very thin to thick while simultaneously controlling the permeability to fluid for imbibition by osmotic device 10. Microporous lamina 23 in one embodiment functions as a support or rigid structure for semipermeable lamina 22, particularly when the latter lamina 22 is thin. Microporous lamina 23 can have preformed micropores, or microporous lamina 23 can contain a microporous pore former, described hereinafter. In this embodiment microporous lamina 23 is formed in situ by exterior fluid wetting and dissolving the pore-former that leaves to form microporous lamina 23. Microporous lamina 23 is permeable to the passage of fluid and the material forming microporous lamina 23, housing the pore-former, maintains its physical and chemical integrity in the environment of use, and it is substantially non-erodible and inert in the environment of use. Additionally, in osmotic device 10 of FIG. 4, microporous lamina 23 houses drug 24 that is available for rapid, initial drug delivery to a drug receptor. Drug 24 can serve as a sole pore-former to form a microporous lamina in embodiment of this invention when the amount of drug is in excess of 40% in lamina 23. Drug 24 can cooperate with a nondrug pore-former for forming a microporous lamina, in embodiments when the combined amount of drug and pore-former excessed 25%, by weight. The delivery of drug 24 from microporous lamina 23 is additional to delivery of drug 16 at a controlled and continuous rate by osmotic device 10.

Figure 5:
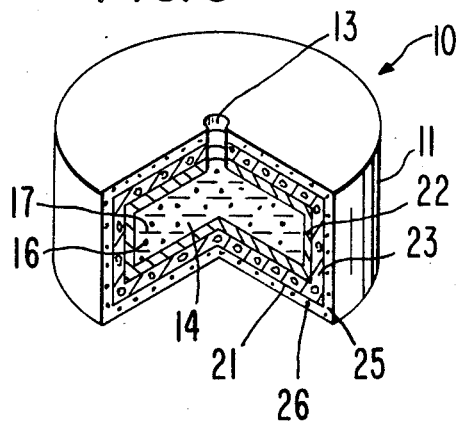
FIG. 5 is an osmotic device with a section removed for depicting the reservoir of the osmotic device and its laminated wall coated with a water-soluble lamina containing drug.

FIG. 5 illustrates, in opened view, an osmotic device 10 that is structurally similar to osmotic device 10 of FIG. 4. In FIG. 5, osmotic device 10 additionally comprises lamina 25 comprising drug 26. Lamina 25 is coated onto the exterior surface of device 10. Lamina 25, the outermost lamina, is formed of an aqueous soluble material, or a material soluble in, or disintegrated by the environment of use, such as the acidic fluid of the stomach. Lamina 25 contains a water-soluble drug 26, or a drug 26 that has limited solubility in the exterior fluids. Lamina 25 releases drug 26 by erosion, dissolution or the like. Lamina 25 provides an initial burst or dosing of drug 26 for raising the blood-plasma level of drug up to a therapeutic level as quickly as possible after the initial dosing of drug 26. The initial dosing of drug 26 can be immediate total drug dosing, or it can be over a period of 15 minutes to 75 minutes. The initial dosing of drug 26 diminishes the time drug is unavailable to a host by supplying drug during the start-up time required for osmotic device 10 to deliver drug. The initial dosing of drug can be supplied in an increased amount also for lessening the effects of in vivo metabolism. The initial dosing is effected without affecting the release kinetics and the rate controlling properties of osmotic device 10.

Figure 6:
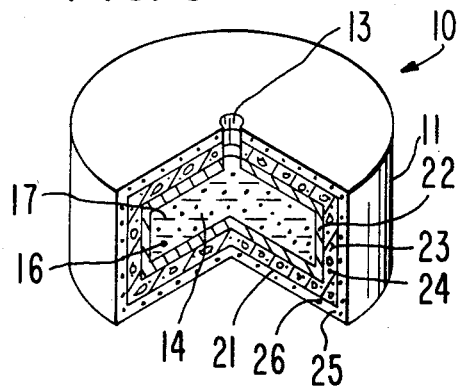
FIG. 6 is an osmotic device in opened section depicting the structure of the device including a microporous lamina containing drug and an outermost water-soluble lamina containing drug.

FIG. 6 illustrates, in opened view, an osmotic device 10 that is an embodiment of device 10 of FIGS. 4 and 5. In FIG. 6, device 10 comprises an outermost lamina 25 containing drug 26 and microporous lamina 23 containing drug 24. Lamina 25 containing drug 26 provides an immediate pulse or large burst of drug 26 followed by microporous lamina 23 providing an increased amount of drug 24. Drug 24 and drug 26 can be the same or different and they are administered for their therapeutic effects.

Figure 7:
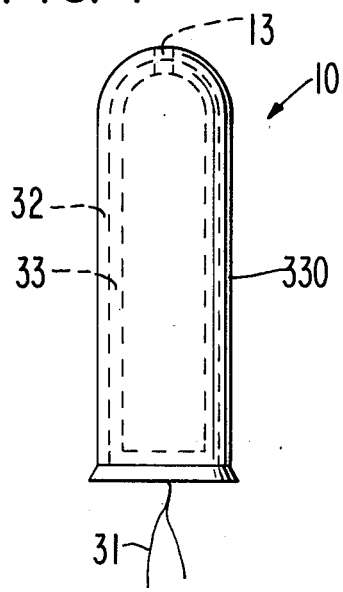
FIG. 7 shows an osmotic device designed for delivering a beneficial drug into a body passageway, such as the ano-rectal and vaginal passageways.
Figure 8:
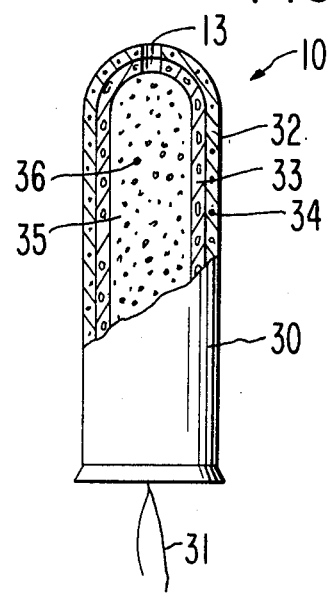
FIG. 8 shows the osmotic therapeutic system of FIG. 7, with its wall partially broken away for elucidating the structural details thereof.

FIGS. 7 and 8 represent another osmotic therapeutic system 10 manufactured according to the invention for administering drug to a drug receptor. In the illustrated embodiment, system 10 is designed for releasing drug in the vagina or the ano-rectal passage, both not shown. System 10 has an elongated-shaped body 30 with a string 31 attached thereto for removing system 10 from a body passageway. System 10 comprises a portal 13 and it is formed with a laminated wall comprising an exterior semipermeable lamina 32 and an interior microporous lamina 33, both seen as dashed lines in FIG. 7, and in opened view in FIG. 8. Semipermeable lamina 32 contains drug 34 available for instant therapy. The amount of drug 34 in semipermeable lamina 32 is from 0.5 to 40% by weight, for maintaining the semipermeable properties of the lamina. The laminated wall surrounds compartment 35 containing drug 36. Osmotic device 10 operated as above described for FIGS. 1 through 6.

FIGS. 1 through 8 are illustrative of various osmotic devices 10 that can be made according to the invention, and it is to be understood these devices are not to be construed as limiting, as the devices can take a wide variety of shapes, sizes and forms adapted for delivering agents to different environments of use. For example, the osmotic device includes buccal, implant, topical, nose, artificial, gland, rectum, cervical, intrauterine, arterial, venous, ear, and the like biological environments. The devices can be adapted also for delivering an active agent in streams, aquariums, fields, factories, reservoirs, laboratory facilities, hot houses, hospitals, veterinary clinics, nursing homes, chemical reactions, and other environments.

DETAILED DESCRIPTION OF THE INVENTION

In accordance with the practice of the invention, it has now been found that osmotic devices can be manufactured with (1) a semipermeable wall containing drug, (2) a semipermeable wall containing drug and coated with a fluid soluble lamina containing drug, (3) a semipermeable wall coated with a fluid soluble lamina containing drug, (4) a laminated wall comprising a semipermeable lamina and a microporous lamina with drug in the microporous lamina, (5) a laminated wall comprising a semipermeable lamina and a microporous lamina containing drug and coated with a fluid soluble lamina containing drug, (6) a laminated wall comprising a semipermeable lamina and a microporous lamina coated with a fluid soluble lamina containing drugs, (7) a microporous lamina and a semipermeable lamina containing drug, and the like.

The semipermeable wall is formed of a material that does not adversely affect the agent or drug, osmagent, an animal host, is permeable to the passage of an external fluid such as water and biological fluids, and it is substantially impermeable to the passage of agents, osmagents, and the like. The selectively semipermeable materials are non-erodible and they are insoluble in fluids. Typical materials for forming wall 12 in one embodiment are cellulose esters, cellulose ethers and cellulose ester-ethers. These cellulosic polymers have a degree of substitution, D.S., on the anhydroglucose unit from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like, Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate-butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like.

Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride), semipermeable polymers exhibiting a fluid permeability of $10^{-5}$ to $10^{-1}$ (cc.mil/cm$^2$.hr.atm) expressed as per atmosphere of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, J. R. and Roff, W. J., 1971, published by CRC Press, Cleveland, Ohio.

The laminated wall comprising a semipermeable lamina and a microporous lamina are in laminar arrangement and they act in concert to form an integral laminated wall, that maintains its physical and chemical integrity and does not separate into lamina throughout the operative agent release history of an osmotic device. The semipermeable lamina is made from the semipermeable polymeric materials presented above, the semipermeable homopolymers, the semipermeable copolymers, and the like.

Microporous lamina suitable for manufacturing an osmotic device generally comprises preformed microporous polymeric materials, and polymeric materials that can form a microporous lamina in the environment of use. The microporous materials in both embodiments are laminated to form the laminated wall. The preformed materials suitable for forming the microporous lamina are essentially inert, they maintain their physical and chemical integrity during the period of agent release and they can be generically described as having a sponge-like appearance that provides a supporting structure for a semipermeable lamina and also provide a supporting structure for microscopic-sized interconnected pores or voids. The materials can be isotropic wherein the structure is homogenous throughout a cross-sectional area, or they can be anisotropic wherein the structure is non-homogenous throughout a cross-sectional area. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 micrometers can be used for making a microporous lamina. The pore size and other parameters characterizing the microporous structure also can be obtained from flow measurements, where a liquid flux, J, is produced by a pressure difference $\Delta P$, across the lamina. The liquid flux through a lamina with pores of uniform radius extended through the membrane and perpendicular to its surface with area A given by the relation 1:

$$J = (N\pi r^4 \Delta P)/(8\eta \Delta x) \tag{1}$$

wherein J is the volume transported per unit time and lamina area containing N number of pores of radius r, $\eta$ is the viscosity of the liquid, and $\Delta P$ is the pressure difference across the lamina with thickness $\Delta x$. For this type of lamina, the number of pores N can be calculated from relation 2, wherein $\epsilon$ is the porosity defined as the ratio of void volume to total volume of the lamina: and A is the cross-sectional area of the lamina containing N pores.

$$N = \epsilon x[A/(\pi r^2)] \tag{2}$$

The pore radius then is calculated from relation 3:

$$r = 8\eta[(J\Delta x \tau)/(A\Delta p \epsilon)] \tag{3}$$

wherein J is the volume flux through the lamina per unit area produced by the pressure difference $\Delta P$ across the lamina, $\eta$, $\epsilon$ and $\Delta x$ have the meaning defined above and $\tau$ is the tortuosity defined as the ratio of the diffusional path length in the lamina to the lamina thickness. Relations of the above type are discussed in *Transport Phenomena In Membranes*, by Lakshminatayanaiah, N, Chapter 6, 1969, published by Academic Press, Inc., New York.

As discussed in this reference on page 336, in Table 6.13, the porosity of the lamina having pore radii r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient $\sigma$ which decreases below 0.5. Microporous lamina with a reflection coefficient $\sigma$ in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates a hydrostatic volume flux, and the reflection coefficient is expressed by relation 4:

$$r = 8\eta \frac{J \Delta x \tau}{A \Delta p \epsilon} \tag{3}$$

Properties of microporous materials are described in *Science*, Vol. 170, pages 1302 to 1305, 1970; *Nature*, Vol. 214, page 285, 1967; Polymer Engineering and Science, Vol. 11, pages 284–288, 1971; U.S. Pat. Nos. 3,567,809 and 3,751,536; and in *Industrial Processing With Membranes*, by Lacey R. E., and Loeb, Sidney, pages 131 to 134, 1972, published by Wiley, Interscience, New York.

Microporous materials having a preformed structure are commercially available and they can be made by art-known methods. The microporous materials can be made by etched nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

Microporous materials useful for making the lamina include microporous polycarbonates comprised of linear polyesters of carbonic acid in which carbonate groups recur in the polymer chain, microporous materials prepared by the phosgenation of a dihydroxyl aromatic such as bisphenol a, microporous poly(vinylchloride), microporous polyamides such as polyhexamethylene adipamide, microporous modacrylic copolymers including those formed from poly(vinylchloride) 60% and acrylonitrile, styrene-acrylic and its copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, microporous poly(saccharides), microporous poly(saccharides) having substituted and unsubstituted anhydroglucose units and preferably exhibiting an increased permeability to the passage of water and biological fluids than semipermeable lamina, asymmetric porous polymers, cross-linked olefin polymers, hydrophobic or hydrophilic microporous homopolymers, copolymers or interpolymers having a reduced bulk density, and materials described in U.S. Pat. Nos. 3,597,752; 3,643,178; 3,654,066; 3,709,774; 3,718,532; 3,803,061; 3,852,224; 3,853,601; and 3,852,388, in British Pat. No. 1,126,849, and in *Chem. Abst.*, Vol. 71 4274F, 22572F, 22573F, 1969.

Additional microporous materials include poly(urethanes), cross-linked, chain-extended poly(urethanes), microporous poly(urethanes) in U.S. Pat. No. 3,524,753, poly(imides), poly(benzimidazoles), collodion (cellulose nitrate with 11% nitrogen), regenerated proteins, semi-solid cross-linked poly(vinylpyrrolidone), microporous materials prepared by diffusion of multivalent cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589; 3,541,055; 3,541,066 and 3,546,142, derivatives of poly(styrene) such as poly(sodium styrenesulfonate) and poly(vinyl benzyltrimethylammonium chloride), the microporous materials disclosed in U.S. Pat. No. 3,615,024 and U.S. Pat. Nos. 3,646,178 and 3,852,224.

Further, the microporous forming material used for the purpose of the invention, includes the embodiment wherein the microporous lamina is formed in situ, by a pore-former being removed by dissolving or leaching it to form the microporous lamina during the operation of the system. The pore-former can be a solid or a liquid. The term liquid, for this invention, embraces semi-solids and viscous fluids. The pore-formers can be inorganic or organic. The pore-formers suitable for the invention include pore-formers that can be extracted without any chemical change in the polymer. The pore-forming solids have a size of about 0.1 to 200 microns and they include alkali metal salts such as sodium chloride, sodium bromide, potassium chloride, potassium sulfate, potassium phosphate, sodium benzoate, sodium acetate, sodium citrate, potassium nitrate and the like. The alkaline earth metal salts include calcium phosphate, calcium nitrate, and the like. The transition metal salts include ferric chloride, ferrous sulfate, zinc sulfate, cupric chloride, manganese fluoride, manganese fluorosilicate, and the like. The pore-formers include organic compounds such as polysaccharides. The polysaccharides include the sugars sucrose, glucose, fructose, mannitol, mannose, galactose, aldohexose, altrose, talose, sorbitol, lactose, monosaccharides and disaccharides. Also, organic aliphatic and aromatic oils, including diols and polyols, as exemplified by polyhydric alcohols, poly(alkylene glycols), polyglycols, alkylene glycols, poly($\alpha$-$\omega$)-alkylenediols esters or alkylene glycols and the like; water soluble cellulosic polymers such as hydroxyloweralkyl cellulose, hydroxypropyl methylcellulose, methyl cellulose, methylethyl cellulose, hydroxyethyl cellulose and the like; water soluble polymers such as polyvinylpyrrolidone, sodium carboxymethylcellulose and the like; and water soluble drugs usually in the form of addition salts such as procainamide hydrochloride, propoxyphene hydrochloride and the like. The pore-formers are nontoxic, and on their removal from the lamina channels are formed through the lamina. In a preferred embodiment, the non-toxic pore-forming agents are selected from the group consisting of inorganic and organic salts, carbohydrates, polyalkylene glycols, poly($\alpha$-$\omega$)-alkylenediols, esters of alkylene glycols, glycols, and water soluble cellulosic polymers, useful for forming a microporous lamina in a biological environment. Generally, for the purpose of this invention, when the polymer forming the lamina contains more than 40% by weight of a pore-former, or a mixture of a pore-former and a drug, the polymer is a precursor microporous lamina that on removing the pore-former, or the pore-former and the drug, yields a lamina which is substantially microporous; at concentrations less than this, the lamina behaves like a semipermeable lamina or membrane. In this latter embodiment the semipermable lamina comprises 0.5 to 40% by weight of drug, or a mixture of drug and pore-former of 0.5 to 40% by weight.

The materials useful for forming a lamina containing drug that is instantly available for immediate therapy include water soluble polysaccharide gums such as carrageenan, fucoidan, gum ghatti, tragacanthin, arabinogalactan, pectin, xanthan, and the like; water-soluble salts of polysaccharide gums such as sodium alginate, sodium tragacanthin, sodium gum ghattate, and the like; water-soluble hydroxyalkylcellulose wherein the alkyl member is straight or branched of 1 to 7 carbons such as hydroxymethylcellulose, hydroxyethylcellulose, hydroxypropylcellulose, and the like; synthetic water-soluble cellulosebased lamina formers such as methyl cellulose and its hydroxyalkyl methylcellulose cellulose derivatives such as a member selected from the group consisting of hydroxyethyl methylcellulose, hydroxypropyl methylcellulose, hydroxybutyl methylcellulose, and the like; and other cellulose polymers such as sodium carboxymethylcellulose. Other lamina forming materials that can be used for this purpose include polyvinyl-pyrrolidone, polyvinylalcohol, polyethylene oxide, a blend of gelatin and polyvinylpyrrolidone, gelatin, glucose, saccharides, and the like.

The expression passageway as used herein comprises means and methods suitable for releasing the agent or drug from the osmotic system. The expression includes aperture, orifice, hole, or bore through the semipermeable wall or the laminated wall. The passageway can be formed by mechanical drilling, laser drilling, or by eroding an erodible element, such as a gelatin plug, in the environment of use. A detailed description of osmotic passageways, and the maximum and minimum dimensions for a passageway are disclosed in U.S. Pat. Nos. 3,845,770 and 3,916,899.

The osmotically effective compounds that can be used for the purpose of the invention include inorganic and organic compounds that exhibit an osmotic pressure gradient against an external fluid across the semipermeable wall or the laminated wall. The osmotically effective compounds are known also as osmotically effective solutes, or osmagents. The compounds are used by mixing them with an agent or drug that has limited solubility in the external fluid with the compounds forming a solution containing agent that is osmotically delivered from the system. The phrase "limited solubility" as used herein means the beneficial agent or drug has a solubility of about less than 1% by weight in the aqueous fluid present in the environment. The osmotic solutes are used by homogenously or heterogenously mixing the solute with the agent or drug, and in one manufacture charging them into the reservoir. The solutes attract fluid into the reservoir producing a solution of solute which is delivered from the system concomitantly transporting undissolved and dissolved beneficial agent to the exterior of the system. Osmotically effective solutes used for the former purpose include magnesium sulfate, magnesium chloride, sodium chloride, lithium chloride, potassium sulfate, sodium sulfate, lithium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixtures thereof.

The osmotic solute is initially present in excess and it can be any physical form such as particle, crystal, pellet, tablet, strip, film or granule. The osmotic pressure of saturated solutions of various osmotically effective compounds and for mixtures of compounds at 37° C., in water, is listed in Table 1. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 1, osmotic pressures of from 20 ATM to 500 ATM are set forth; of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by the Hewlett Packard Co., Avandale, Penna.

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Dextrose | 82 |
| Potassium Sulfate | 39 |
| Mannitol | 38 |
| Sodium Phosphate Tribasic.12H$_2$O | 36 |
| Sodium Phosphate Dibasic.7H$_2$O | 31 |
| Sodium Phosphate Dibasic.12H$_2$O | 31 |
| Sodium Phosphate Dibasic Anhydrous | 29 |
| Sodium Phosphate Monobasic.H$_2$O | 28 |

The expression "active agent" as used herein broadly includes any compound, or mixture thereof, that can be delivered from the system to produce a beneficial result. The agent can be soluble in fluid that enters the reservoir and functions as an osmotically effective solute or it can have limited solubility in the fluid and be mixed with an osmotically effective soluble soluble in fluid that is delivered from the system. The active agent used herein includes also any compounds that can be delivered from the wall for immediate therapy. The active and beneficial agents nclude pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promotors, air purifiers, micro-organism attenuators, and other agents that benefit that environment of use.

In the specification and the accompanying claims, the term "drug" includes any physiologically or pharmacologically active substances that produce a localized or systemic effect or effects in animals, which term includes mammals, humans and primates. The term also includes domestic household, sport or farm animals such as sheep, goats, cattle, horses and pigs, for administering to laboratory animals such as mice, rats and guinea pigs, and to fishes, to avians, to reptiles and zoo animals. The term "physiologically" as used herein denotes the administration of drug to produce normal levels and functions. The term "pharmacologically" denotes variations in response to amounts of drug including therapeutics as defined in Stedman's Medical Dictionary, 1966, published by Williams & Wilkins, Baltimore, Md. The phrase drug formulation as used herein means the drug is in the compartment by itself, or the drug is in the compartment mixed with an osmotic solute, binder, dye, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synoptic sites, neuroeffector junctional sites, endocrine and hormone systems, immunological system, reproductive system, skeletal system, autocoid systems, alimentary and excretory systems, inhibitory of autocoids and histamine systems. The active drug that can be delivered for acting on these animal systems includes depressants, hypnotics, sedatives, psychic energizers, tranquilizers, anticonvulsants, muscle relaxants, antiparkinson agents, analgesics, anti-inflammatory, local anesthetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents and cardiovascular drugs.

Drugs that act on the central nervous system include hypnotics and sedatives, including pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and α-bromoisovaleryl urea; hypnotic and sedative urethanes and disulfanes; psychic energizers such as isocoboxazid, nialamide, phenelzine, imipramine, tranylcypromine and parglyene; tranquilizers such as chloropromazine, promazine, fluphenazine, reserpine, deserpidine, meprobamate, and benezodiazepines such as chlordiazepoxide; anticonvulsants such as primidone, enitabas, diphenylhydantion, ethltion, pheneturide and ethosuximide; muscle relaxants and antiparkinson agents such as mephenesin, methocarbomal, trihexlphenidyl, and biperiden; anti-hypertensives such as methyl dopa and L-β-3-4-dihydroxypenhnylalanine, and pivaloyloxyethyl ester of α-methyldopa hydrochloride dihydrate; analgesics such as morphine, codeine, meperidine, nalorphine, antipyretics and anti-inflammatory agents such as aspirin, indomethacin, salicylamide, naproxen, colchicine fenoprofen, sulidac, diclofenac, indoprofen and sodium salicylamide, local anesthetics such as procaine, lidocaine, maepaine, piperocaine, tetracaine and dibucane; antispasmodics and muscle contractants such as atropine, scopolamine, methscopolamine, oxyphenonium, papaverine; prostaglandins such as $PGE_1$ $PGE_2$, $PGF_{1\alpha}$, $PGF_{2\alpha}$ and PGA; anti-microbials such as penicillin, tetracycline, oxytetracycline, chlorotetracycline, chloramphenicol and sulfonamides; anti-malarials such as 4-aminoquinolines, 8-aminoquinolines and pyrimethamine; hormonal agents such as prednisolone, cortisone, cortisol and triamcinolone; androgenic steroids such as methyltesterone, and fluoxmesterone; estrogenic steroids such as $17\beta$-estradiol, $\alpha$-estradiol, estriol, $\alpha$-estradiol 3-benzoate, and 17-ethynyl estradiol-3-methyl ether; progestational steroids such as progesterone, 19-nor-pregn-4-ene-3,20-dione, 17-hydroxy-19-nor-17-$\alpha$-pregn-5(10)-ene-20-yn-3-one, 17$\alpha$-ethynyl-17-hydroxy-5(10)-estren-3-one, and $9\beta,10\alpha$-pregna-4,6-diene-3,20-dione; sympathomimetic drugs such as epinephrine, amphetamine, ephedrine and norepinephrine; hypotensive drugs such as hydralazine, cardiovascular drugs such as procainamide, procainamide hydrochloride, amyl nitrite, nitroglycerin, dipyredamole, sodium nitrate and mannitol nitrate; diuretics such as chlorathiazide, acetazolamide, methazolamide and flumethiazide; antiparasitics such as bephenium, hydroxynaphthoate, dichlorophen and dapsone; and neoplastics such as nechlorethamine, uracil mustard, 5-fluorouracil, 6-6-thioguanine and procarbazine; $\beta$-blockers such as pindolol, propranolol, practolol, metoprolol, oxprenolol, timolol, atenolol, alprenolol, and acebutolol; hypoglycemic drugs such as insulin, isophane insulin, protamine zinc insulin suspension, globin zinc insulin, extended insulin zinc suspension, toblutamide, acetohexamide, tolazamide and chlorpropamide; antiulcer drugs such as cimetidine; nutritional agents such as ascorbic acid, niacin, nicotinamide, folic acid, choline, biotin, pantothenic acid, and vitamin $B_{12}$; essential amino acids; essential fats; eye drugs such as pilocarpine, pilocarpine salts such as pilocarpine nitrate, pilocarpine hydrochloride, dichlophenamide, atropine, atropine sulfate, scopolamine and eserine salicylate; histamine receptor antagonists such as cimetidine; and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate; and drugs that act on $\alpha$-adrenergic receptors such as clonidine hydrochloride. The beneficial drugs are known to the art in *Remington's Pharmaceutical Sciences,* 14th Ed., 1970, published by Mack Publishing Co., Easton, Penna.; and in *The Pharmacological Basis of Therapeutics,* by Goodman and Gilman, 4th Ed., 1970, published by The MacMillan Company, London.

The drug can be in various forms, such as uncharged molecules, molecular complexes, pharmacologically acceptable salts such as hydrochlorides, hydrobromides, sulfate, laurylate, palmitate, phosphate, nitrite, nitrate, borate, acetate, maleate, tartrate, oleate, and salicylate. For acid drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir compartment as a dispersion, paste, cream, particle, granule, emulsion, suspension or powder. Also, the agent can be mixed with a binder, dispersant, emulsifier or wetting agent, lubricant, and dyes.

The amount of agent present in the system is initially in excess of the amount that can be dissolved in the fluid that enters the reservoir. Under this physical state when the agent is in excess, the system will osmotically operate to give a substantially constant rate of release. The rate of release can also be varied by having different amounts of agent in the reservoir to form solutions containing different concentrations of agent for delivery from the device. Generally, the system can house from 0.05 ng to 5 grams or more, with individual systems containing for example, 25 ng, 1 mg, 5 mg, 125 mg, 250 mg, 500 mg, 750 mg, 1.5 g, and the like. The amount of drug in a semipermeable wall usually is 0.5 ng up to 50 mg, in a microporous lamina usually about 0.5 mg up to 85 mg, and the amount in a water soluble lamina is about 0.5 ng up to 85 mg. The osmotic device can be administered once, twice or thrice daily.

The solubility of an agent in the fluid can be determined by known techniques. One method consists of preparing a saturated solution comprising the fluid plus the agent as ascertained by analyzing the amount of agent present in a definite quantity of the fluid. A simple apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin,* No. 67 of the Hygenic Laboratory; *Encyclopedia of Schience and Technology,* Vol. 12, pages 542 to 556, 1971, published by McGraw-Hill, Inc.; and *Encyclopedia Dictionary of Physics,* Vol. 6, pages 547 to 557, 1962, published by Pergamon Press, Inc.

The systems of the invention are manufactured by standard techniques. For example, in one embodiment, the agent and other ingredients that may be housed in the compartment and a solvent are mixed into a solid, semisolid or gel form by conventional methods such as ballmilling, calendering, stirring, or rollmilling and then pressed into a preselected shape. The laminae forming the system can be applied by molding, spraying or dipping the pressed shape into wall forming materials. In another embodiment, the laminae can be cast into films, shaped to the desired dimensions, an exterior lamina sealed to an interior lamina to define a compartment that is filled with agent and then closed. The system also can be manufactured with an empty compartment that is filled through the passageway. The system, when formed of more than one laminate, is joined by various joining techniques, such as high frequency electronic sealing that provides clean edges and a firmly sealed system. Another, and presently preferred technique that can be used to apply laminate to a compartment is the air suspension procedure. This procedure consists in suspending and tumbling the pressed agent in a current of air and a lamina composition until the lamina is applied to the agent. The procedure is repeated with a different lamina to form the laminate. The air suspension procedure is described in U.S. Pat. No. 2,799,241; *J Am. Pharm. Assoc.*, Vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, 14th Edition, pages 1626 to 1678, 1970, published by Mack Publishing Co., Easton, Penna.

Exemplary solvent suitable for manufacturing the laminates and laminae include inert inorganic and organic solvents that do not adversely harm the materials and the final laminated wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate ethyl acetate, isopropyl acetate, n-butyl acetate, methyl isobutyl ketone, methyl propyl keton, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benezene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery system manufactured as an osmotic device shaped, sized and adapted as an osmotic tablet for oral admittance into the gastrointestinal tract is manufactured as follows: first, 53 g of sodium indomethacin trihydrate is blended with 47 g of mannitol and 33 g of water into a homogenous blend. The ingredients are blended in a small laboratory blender for 30 minutes, and then the blend is passed through a 20 mesh screen. Next, the screened, homogenous blend is dried in an oven at 50° C. for about 2 hours, removed from the oven and passed through a 10 mesh screen. The latter screened granules are returned to the oven and dried at 50° C. for an additional 2 hours. Next, the dried granulation is mixed with 2% by weight of magnesium stearate and pressed into a number of drug cores with a standard tablet machine. The compressed drug cores each have a diameter of about 6.5 mm and weight of 190 mg. The drug cores are next coated with a semipermeable wall-forming composition containing sodium indomethacin trihydrate. The composition comprises 13 g of sodium indomethacin trihydrate and 117 g of cellulose acetate having an acetyl content of 32%. The wall is formed from a solvent system comprising 260 ml of water and 2900 ml of acetone. A Wurster air suspension coater is used to form the semipermeable wall containing the anti-inflammatory drug. The solvent is evaporated in a circulating air oven at 50° C. for 65 hours, and after cooling to room temperature a 0.25 mm diameter passageway is laser drilled through the semipermeable wall. The passageway connects the exterior of the osmotic device with the drug compartment for releasing drug. The final osmotic device contained 52% sodium indomethacin trihydrate, 46% mannitol and 2% magnesium stearate in the compartment and the semipermeable wall consists of 90% of cellulose acetate having an acetyl content of 32%, and 10% sodium indomethacin trihydrate. The percents are weight percent.

EXAMPLE 2

Figure 9:
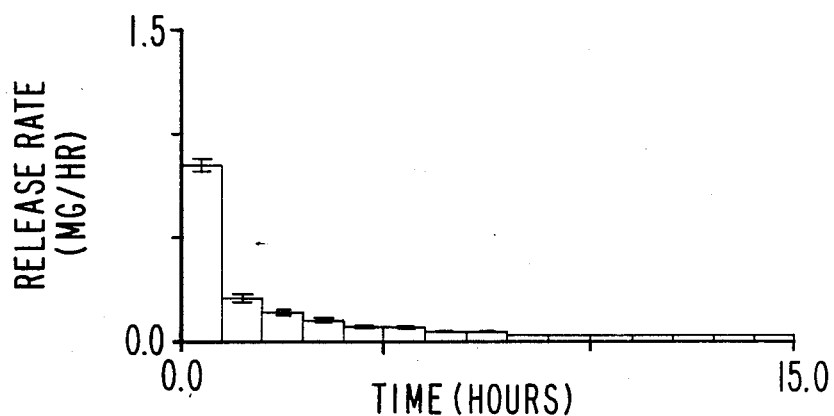
FIG. 9 is a bar graph that depicts the release rate profile for a drug from a semipermeable wall of an osmotic device.

A series of osmotic devices manufactured as oral osmotic tablets are made for demonstrating the release of drug from a semipermeable wall surrounding a compartment as follows: first, 3500 g of potassium chloride is mixed in a blender with 17.5 g of silicon dioxide and 1.75 g of magnesium stearate for about 30 minutes. The blending is carried out at room temperature. Next, the blend is converted to 11 mm diameter drug cores by charging the blend into the cavities of a tablet press, and a compression force of 1 ton applied across a punch to compress the drug. The drug cores next are coated with a composition comprising cellulose acetate having an acetyl content of 32% and sodium indomethacin trihydrate. The semipermeable wall formed consists of 88.5% cellulose acetate having an acetyl content of 32% and 11.5% sodium indomethacin trihydrate. The semipermeable wall is 0.3 mm thick and a 0.25 mm diameter passageway is laser drilled through the semipermeable wall. The release rate in water in mg/hr of sodium indomethacin from the semipermeable wall measured by UV absorbance is seen in FIG. 9.

EXAMPLE 3

An osmotic, therapeutic device for the instant release and the controlled and continuous release for oral administration of a beneficial appetite suppressant is manufactured as follows: first, 2,284.8 g of the sympathomimetric, anorectic drug phenylpropanolamine hydrochloride is passed through a number 30 mesh screen and transferred to a blending bowl. Next, 91.2 g of hydroxypropyl methylcellulose is added to 510 ml of ethanol-water system 84:16 by volume in a separate blender and blended until a clear solution is produced. Then, the hydroxypropyl methylcellulose-ethanol-water solution is added to the phenylpropanolamine hydrochloride and blended for 1 hour to produce an even consistency. Next, the wet granulation is passed through a number 30 stainless steel mesh screen, the granules spread on a tray, and dried in a forced air oven at 50° C.±2° C. The granules are dried for 20 to 25 hours, and after cooling to room temperature of 22.2° C. the dried granules are passed through a number 20 stainless steel sieve. The granulation is returned to the blending bowl and 24 g of stearic acid, previously passed through a number 80 stainless steel sieve, is added to the bowl and all the ingredients blended on low speed for 10 minutes. Finally, a number of drug formulations, which became the drug reservoirs of the osmotic device, are made by compressing the drug formulation containing all the ingredients in a 6 mm die cavity under a compression load of 900 kg. The final drug formulation consists essentially of 55 mg of phenylpropanolamine hydrochloride, 2.5 mg of hydroxypropyl methylcellulose and 0.6 mg of stearic acid.

Figure 10:
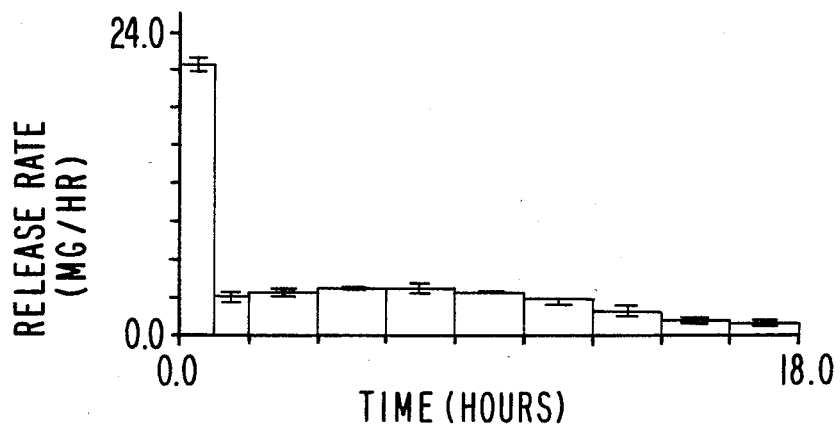
FIG. 10 depicts the release rate profile for an osmotic device made according to the invention.
Figure 11:
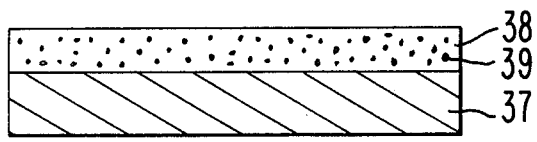
FIG. 11 illustrates a laminate structure comprising a semipermeable lamina laminated to a lamina containing drug for quick release.

Next, a semipermeable wall is formed around the drug cores by blending 150 g of cellulose acetate having an acetyl content of 39.8% with 2493 ml of methylene chloride and 456 ml of methanol and spray coating the semipermeable wall forming composition around the drug cores in a conventional air suspension coater. The wall forming coating is continued until all the coating solution is used, usually over a period of 1 to 2 hours. Then, a second laminate forming composition comprising 352 g of dry phenylpropanolamine hydrochloride and 88 g of dry hydroxypropyl methylcellulose in a solvent system comprising 2842 ml of methylene chloride and 2578 ml of methanol is prepared by adding the drug ingredients to the solvent system with continual mixing for 30 minutes to produce a clear laminate forming solution. The solution is added to the air suspension coater and a laminate is coated onto the semipermeable wall. Finally, the coated osmotic devices are placed on stainless steel trays and dried at 50° C. for 48 hours, and then an osmotic passageway is laser drilled through the laminated wall. The osmotic passageway has a diameter of about 0.25 mm. FIG. 10 depicts the release rate profile for osmotic devices provided according to this example. The osmotic devices provide first a therapeutically effective initial pulse dose of drug over a short delivery period accompanied by a therapeutically effective amount of drug delivered at a controlled rate and continuously over a prolonged period of time. FIG. 11 depicts a laminated structure made according to the example. The laminate also could be made by solvent casting of the laminae. The laminate comprises a semipermeable lamina 37 formed of a cellulose acylate that maintains its physical integrity in aqueous and biological environments, which lamina 37 is in laminar arrangement with a lamina 38 formed of a material that looses its physical integrity in an aqueous or biological environment. Lamina 38 contains drug 39 that is released from lamina 38 as it changes its integrity.

EXAMPLE 4

A therapeutic, osmotic device, adapted and shaped as an osmotic tablet for administering orally a therapeutically effective amount of the histamine $H_2$ receptor antagonist cimetidine hydrochloride for the management of daytime and nocturnal basal gastric acid secretion and its accompanying ulcers is manufactured as follows: a multiplicity of drugforming reservoirs each containing 740 mg of cimetidine hydrochloride, 32 mg of polyvinyl pyrrolidone, 16 mg of cross-linked sodium carboxymethylcellulose and 8 mg of magnesium stearate are formed by first blending the polyvinyl pyrrolidone with an ethanol-water solvent, 70-30, vol-vol, for about 15-20 minutes to produce a solution. Separately, the sodium carboxymethylcellulose and the cimetidine hydrochloride are blended, passed through a number 40 mesh sieve. Then the polyvinyl pyrrolidone solution is added in small increments to the carboxymethylcellulose-cimetidine homogenous blend in a blender bowl, and all the ingredients blended for 20-25 minutes to produce a blend having the consistency of wet paste. The wet paste is passed through a number 10 sieve and the screened granules dried for 24 hours at 50° C. The dried granules are passed through a 20 mesh screen, and the magnesium stearate mixed therewith. The blending is continued for 5 to 10 minutes, and the final blend fed to a die and punched into drug forming reservoir cores, having an elliptical shape measuring ¾ inches, 20 mm, across its longest axis.

Next a semipermeable wall is formed around the drug cores by coating the drug cores with a semipermeable wall forming composition comprising: in percent by weight: 29.2% cellulose acetate having an acetyl content of 32%; 30.8% cellulose acetate having an acetyl content of 39.8%; 20% cimetidine hydrochloride; 14% hydroxypropyl methylcellulose; and, 6% polyethylene glycol 4000, in an 80% methylene chloride 20% methanol solvent system. The drug cores are coated in an air suspension machine until all the coating solution is used, requiring usually 1 to 2 hours. The final semipermeable wall surrounding the drug core weighed about 50 mgs, and was about 0.12 mm thick. A 0.26 mm exit port is laser drilled through the semipermeable wall. In operation in a fluid environment, the osmotic device delivers drug from the wall and from the drug reservoir through the exit port to a biological drug receptor.

EXAMPLE 5

Figure 12:
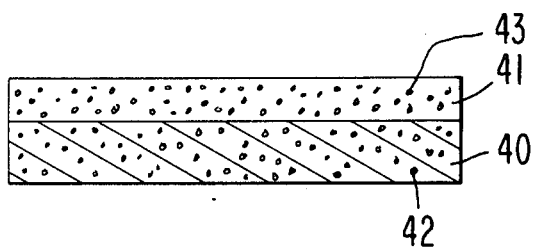
FIG. 12 depicts a laminate comprising a semipermeable lamina containing drug in laminar arrangement with water soluble lamina containing drug.

The procedure of Example 4 is repeated with the device made as described, and in this example an outermost lamina is laminated onto the semipermeable wall. The outermost lamina is water soluble and it comprises 80% cimetidine hydrochloride monohydrate and 20% hydroxypropyl methylcellulose. The lamina is laminated onto the semipermeable wall in an air suspension coating machine with a methylene chloride-methanol solvent, in a 75% to 25% vol to vol ratio. An osmotic exit port is laser drilled through the laminated wall. In operation, in a fluid environment, the outermost water soluble wall instantly delivers a pulse amount of drug, followed by drug delivered from the semipermeable wall and from the drug reservoir through the osmotic port. FIG. 12 depicts the laminated wall provided by this example. The laminate comprises a semipermeable lamina 40 in laminar arrangement with a water soluble lamina 41. Lamina 40 is formed of a member selected from the group consisting of cellulose acylate, cellulose diacylate and cellulose triacylate having drug 42 dispersed therein, and lamina 41 is formed of a water soluble member selected from the group consisting of methyl cellulose, hydroxypropyl methylcellulose, polyvinyl-pyrrolidone and polyvinylalcohol containing drug 43. The laminate also can be made by successive casting of the laminae.

EXAMPLES 6-7

Figure 13:
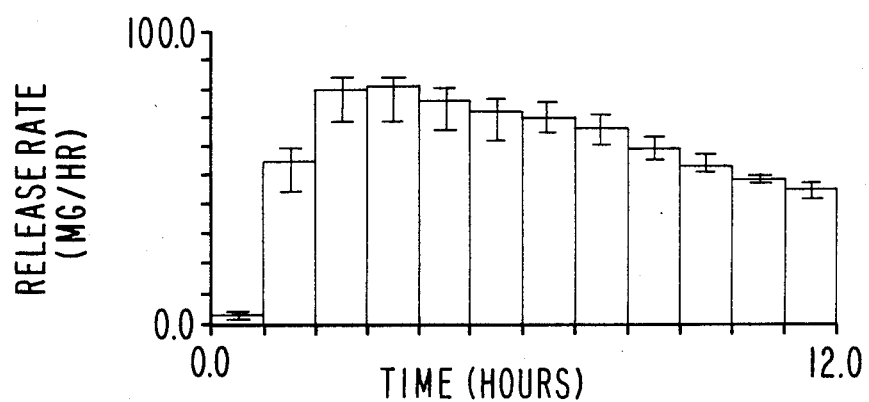
FIG. 13 depicts the release of drug from an osmotic device over a prolonged period of time.
Figure 14:
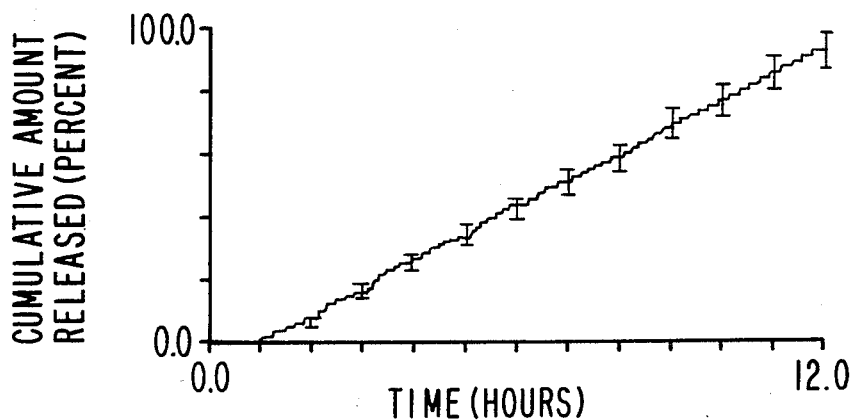
FIG. 14 depicts the cumulative amount of drug released by the osmotic device of FIG. 13.

The procedure of Examples 4 and 5 are repeated in this example. The osmotic devices produced by this example comprised of drug core consisting essentially of 94% cimetidine hydrochloride monohydrate, 4% polyvinylpyrrolidone and 2% magnesium stearate; a microporous lamina adjacent to and surrounding the reservoir, comprising 45% cellulose acetate having an acetyl content of 39.8%, 27.5% polyethylene glycol 4000, and 27.5% hydroxypropylmethylcellulose; and a semipermeable lamina distant from the drug and in laminar arrangement with the microporous lamina, the semipermeable lamina comprising 29.8% cellulose acetate having an acetyl content of 32%, 10.2% cellulose acetate having an acetyl content of 39.8%, and 20% hydroxypropyl methylcellulose. The diameter of the passageway is 0.26 mm. FIG. 13 depicts the release rate from this device and FIG. 14 depicts the cumulative amount released over time from the same device.

Figure 15:
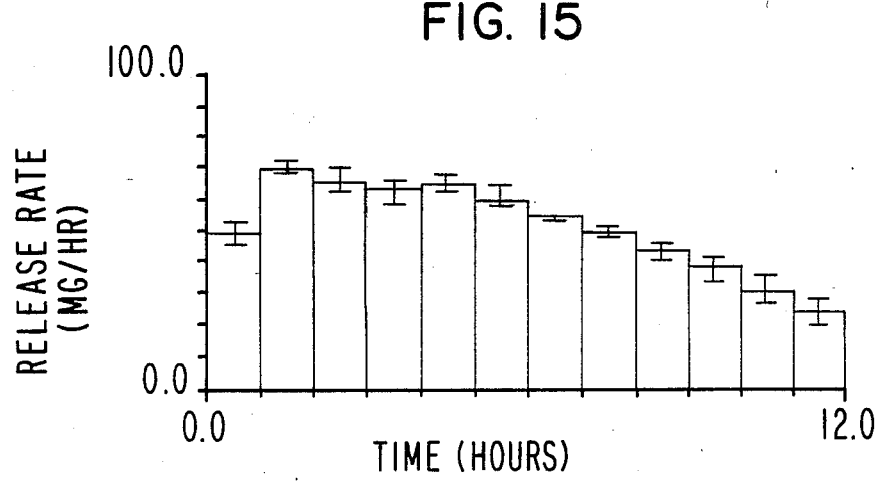
FIG. 15 depicts a pulsed release of drug accompanied by prolonged release of drug from an osmotic device.
Figure 16:
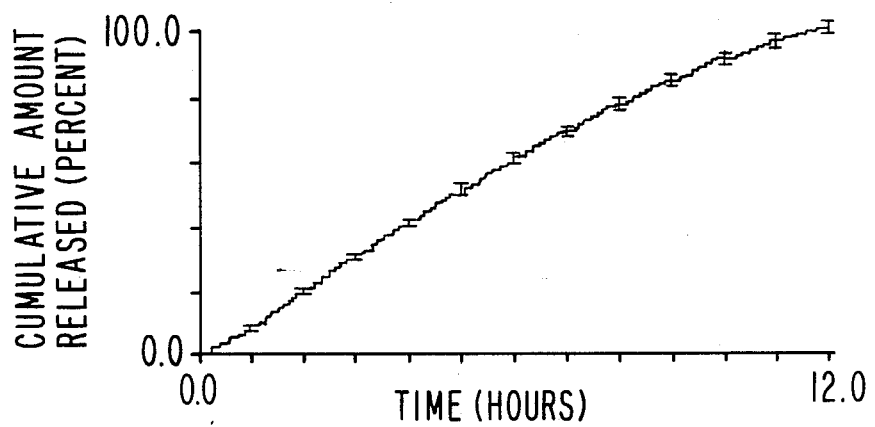
FIG. 16 depicts the cumulative amount of drug released from the osmotic device of FIG. 15 over time.

An osmotic device comprising drug in its outer lamina is prepared as described with the device consisting essentially of the following: a drug core consisting essentially of 94% cimetidine hydrochloride monohydrate, 4% polyvinylpyrrolidone, and 2% magnesium stearate; a microporous lamina adjacent to and surrounding the reservoir comprising 45% cellulose acetate having an acetyl content of 39.8%, 27.5% hydroxypropyl methylcellulose, and 27.5% polyethylene glycol 4000; and a semipermeable lamina distant from the drug reservoir consisting essentially of 69.8% cellulose acetate having an acetyl content of 32%, 10.2% cellulose acetate having an acetyl content of 39.8% and 20% cimetidine hydrochloride monohydrate. The diameter of the passageway is 0.26 mm. FIG. 15 depicts the pulse release of drug from the lamina and the release rate through the passageway from the device. FIG. 16 depicts the cumulative amount released from the lamina and the drug reservoir through the passageway over time.

EXAMPLE 8

The procedure of Examples 4 and 5 are followed in this example for manufacturing an osmotic device having a drug reservoir weighing 720 mg. The drug reservoir comprised 94% cimetidine hydrochloride monohydrate, 4% polyvinylpyrrolidone, and 2% magnesium stearate. The semipermeable wall surrounding the drug reservoir comprised 78.5% cellulose acetate having an acetyl content of 32%, 11.5% cellulose acetate having an acetyl content of 39.8% and 10% cimetidine hydrochloride monohydrate. The semipermeable wall was 2 mil (0.05 mm) thick and the diameter of the passageway was 0.26 mm. The device delivered 45 mg of cimetidine during the first hour, including 2 mg from the wall and it had an average delivery rate of about 35 mg of cimetidine per hour over a prolonged period of 12 hours.

EXAMPLE 9

Figure 17:
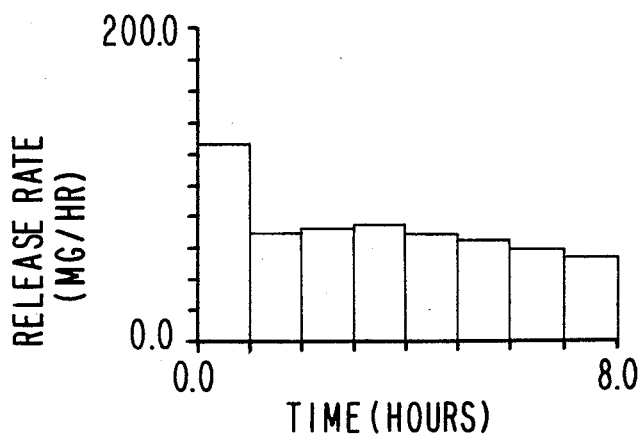
FIG. 17 depicts the release profile for another osmotic device made in the form of an osmotic tablet.
Figure 18:
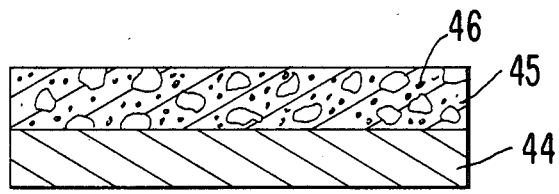
FIG. 18 depicts a laminate comprising a microporous lamina containing drug laminated to a semipermeable lamina.

The procedure of Examples 4 and 5 are followed in this example, for manufacturing an oral osmotic device having a drug reservoir weighing 776 mg. The drug reservoir comprised 94% cimetidine hydrochloride monohydrate present as 77.3% cimetidine and 16.7% hydrochloride monohydrate, 4% polyvinylpyrrolidone and 2% magnesium stearate. The wall surrounding the reservoir comprised an inner semipermeable lamina consisting of 69.8% cellulose acetate having an acetyl content of 32%, 10.2% cellulose acetate having an acetyl content of 39.8%, and 20% hydroxypropyl methylcellulose in laminar arrangement with an outer microporous wall consisting essentially of 28% cellulose acetate having an acetyl content of 39.8%, 2% hydroxypropylmethylcellulose, and 70% cimetidine hydrochloride monohydrate. The diameter of the passageway was 0.26 mm, the semipermeable wall was 0.04 mm thick, and the microporous wall was 0.24 mm thick. The release rate profile is illustrated in FIG. 17. In FIG. 18, a laminate is depicted comprising semipermeable lamina 44, and microporous lamina 45 containing drug 46.

EXAMPLE 10

Figure 19:
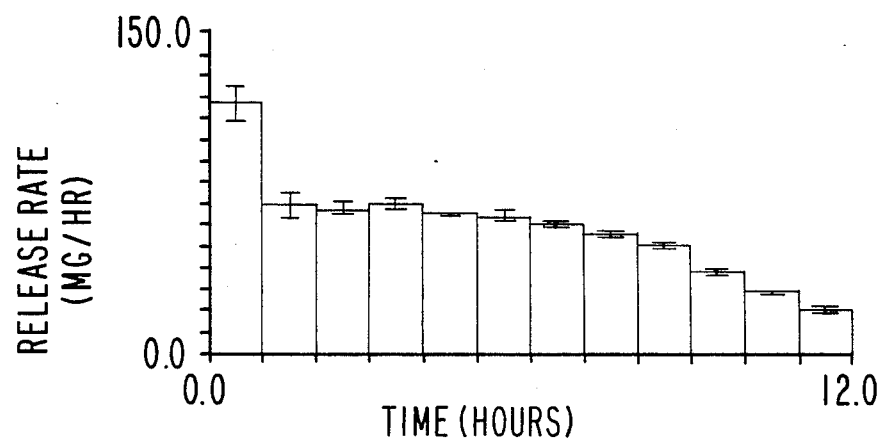
FIG. 19 depicts the release rate profile for an osmotic device comprising a laminate formed of three lamina, a semipermeable lamina, a microporous lamina containing drug, and a water-soluble lamina containing drug.
Figure 20:
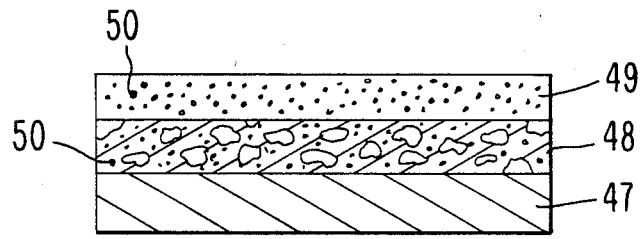
FIG. 20 depicts a laminate comprising a semipermeable lamina, a microporous lamina containing drug, and a water soluble lamina containing drug.
Figure 21:
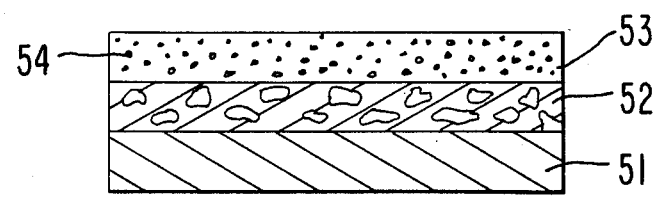
FIG. 21 depicts a laminate comprising a semipermeable lamina, a microporous lamina, and a water soluble lamina containing drug.

The procedure of Examples 4 and 5 are followed for producing an osmotic device comprising a drug reservoir weighing 946 mg and consisting essentially of 94% cimetidine hydrochloride monohydrate, 4% polyvinylpyrrolidone, and 2% magnesium stearate; an inner semipermeable lamina consisting essentially of 69.8% cellulose acetate having an acetyl content of 32%, 10.2% cellulose acetate having an acetyl content of 39.8% and 20% hydroxypropyl methylcellulose; a middle microporous lamina consisting essentially of 45% cellulose acetate having an acetyl content of 39.8% and 55% cimetidine hydrochloride monohydrate; and an outer water dissolvable lamina consisting essentially of 80% cimetidine hydrochloride monohydrate and 20% hydroxypropyl methylcellulose. The diameter of the passageway was 0.26 mm. The release rate for the device is illustrated in FIG. 19. The laminate provided by the invention is seen in FIG. 20, comprising semipermeable lamina 47, microporous lamina 48 and water dissolvable lamina 49. Lamina 48 and lamina 49 contain instant releasable drug 50. FIG. 21 illustrates a laminate comprising a semipermeable lamina 51, microporous lamina 52 and water dissolvable lamina 53 containing drug 54.

EXAMPLE 11

The above procedures are repeated with all procedures as described except that drug reservoir and the lamina contain ranitidine hydrochloride.

The present invention provides many advantages to the medical and veterinary art as described in detail above. The present invention also provides a method for lessening the loss of drug in an animal needing the drug by providing an initial burst of drug for diminishing the loss of drug arising from the transit of drug in the gastrointestional tract and for diminishing the loss of drug arising from metabolism of drug in the liver. Concomitantly, the present invention provides a method for increasing the therapeutically effective amount of drug available for producing a physiological or pharmacological bioaffecting result in an animal by providing drug for lessening in vivo loss, commonly attributed to first-pass effect, while simultaneously providing drug for producing the intended drug result in management of health and disease. Obviously, many modifications and variations of the instant invention are possible in the light of the above teachings. It is therefore to be understood that within the scope of the disclosure and appended claims, the invention may be practiced otherwise than is described specifically herein.

We claim:

1. An osmotic device for delivering a beneficial agent to an environment of use, the osmotic device comprising:
   (a) a wall at least in part formed of a substantially inert material which surrounds and forms a compartment containing a beneficial agent formulation, said substantially inert material being permeable to the passage of an exterior fluid present in the environment of use and substantially impermeable to the passage of the beneficial agent in the compartment;
   (b) a beneficial agent in the wall, said agent being released from the wall when the osmotic device is in operation in a fluid environment of use; and,
   (c) an osmotic passageway in the wall communicating with the compartment and the exterior of the device for dispensing the beneficial agent from the compartment when the device is in the environment of use wherein fluid passes through the wall, causes the formation of an osmotic pressure gradient across the wall and dispenses the beneficial agent from the compartment to the environment via the osmotic passageway.

2. The osmotic device for delivering the beneficial agent according to claim 1, wherein the wall is formed of a semipermeable material containing the beneficial agent that is released therefrom in a pulsed amount.

3. The osmotic device for delivering the beneficial agent according to claim 1, wherein the wall is a laminate that surrounds the compartment and comprises a semipermeable lamina adjacent to the compartment, and a microporous lamina in laminar arrangement with the semipermeable lamina and distant from the compartment, which microporous lamina contains a beneficial agent that is released therefrom in pulsed amount.

4. The osmotic device for delivering the beneficial agent according to claim 1, wherein the wall is a laminate that surrounds the compartment and comprises a semipermeable lamina adjacent to the compartment, and a water soluble lamina in laminar arrangement with the semipermeable lamina distant from the compartment, which water soluble lamina contains a beneficial agent that is released therefrom in a pulsed amount.

5. The osmotic device for delivering the beneficial agent according to claim 1, wherein the wall is a laminate that surrounds the compartment and comprises a semipermeable lamina adjacent to the compartment containing a beneficial agent that is released therefrom in a pulsed amount, and a water soluble lamina in laminar arrangement distant from the compartment that contains a beneficial agent that is released therefrom in a pulsed amount.

6. The osmotic device for delivering the beneficial agent according to claim 1, wherein the beneficial agent is released from the wall in a short period of time and from the compartment over a prolonged period of time.

7. The osmotic device for delivering the beneficial agent according to claim 1, wherein the wall is a laminate that surrounds the compartment and comprises an inner semipermeable lamina, a middle microporous lamina, and an outer water soluble lamina containing beneficial agent that is released therefrom in a short period of time.

8. The osmotic device for delivering the beneficial agent according to claim 1, wherein the wall is a laminate that surrounds the compartment and comprises an inner lamina formed of a semipermeable material, a middle lamina formed of a microporous material containing a beneficial agent that is released therefrom in a short period of time, and an outer lamina formed of a water soluble material containing a beneficial agent that is released therefrom in a short period of time.

9. The osmotic device for delivering the beneficial agent according to claim 7, wherein the beneficial agent is released from the outer lamina in a short pulsed period of time followed by the beneficial agent released from the middle lamina.

10. The osmotic device for delivering the beneficial agent according to claim 1, wherein the beneficial agent is released from the wall concomitantly with beneficial agent being delivered through the passageway from the device.

11. The osmotic device for delivering the beneficial agent according to claim 1, wherein the beneficial agent is released from the wall followed by delivery through the osmotic passageway from the device.

12. An osmotic device for the controlled delivery of a beneficial drug to a biological environment of use, the osmotic device comprising:

(a) a shaped wall at least in part formed of a substantially inert semipermeable material, which surrounds and forms a compartment containing a drug formulation, said substantially inert material being permeable to the passage of a fluid present in the environment of use, and substantially impermeable to the passage of the drug in the compartment;

(b) a beneficial drug carried by the shaped wall that is released therefrom when the device is in operation in the environment of use,;

(c) the drug formulation in the compartment exhibiting an osmotic pressure gradient across the shaped wall against a fluid present in the environment of use, said drug formulation comprising a dosage amount of drug; and, (d) a passageway in the wall connecting the compartment with the exterior of the osmotic device for delivering drug formulation from the compartment to the environment of use wherein fluid passes through the wall, causes the formation of an osmotic pressure gradient across the wall and dispenses the drug from the compartment to the environment via the passageway.

13. The osmotic device for delivering the beneficial agent according to claim 12, wherein the compartment contains an osmagent.

14. The osmotic device for the controlled delivery of the beneficial drug according to claim 12, wherein the wall is at least in part formed of a semipermeable material that is a member selected from the group consisting of cellulose acylate, cellulose diacylate, cellulose triacylate, cellulose acetate, cellulose diacetate, and cellulose triacetate.

15. The osmotic device for the controlled delivery of the beneficial drug according to claim 12, wherein the beneficial drug is cimetidine.

16. The osmotic device for the controlled delivery of the beneficial drug according to claim 12, wherein the beneficial drug is ranitidine.

17. The osmotic device for the controlled delivery of the beneficial drug according to claim 12, wherein the beneficial drug is phenylpropanolamine.

18. The osmotic device for the controlled delivery of the beneficial drug according to claim 12, wherein the environment of use is the gastrointestinal tract.

19. The osmotic device for the controlled delivery of the beneficial drug according to claim 12, wherein the environment of use is a human.

20. The osmotic device for the controlled delivery of the beneficial drug according to claim 12, wherein the device is adapted and sized for oral use in a warm-blooded animal, and when in operation, the device released drug from the wall and imbibed fluid through the wall into the compartment in a tendency towards osmotic equilibrium at a rate controlled by the wall and the osmotic pressure gradient across the wall producing a drug formulation solution that is dispensed from the device at a controlled rate and continuously over a prolonged period of time.

21. The osmotic device for delivering a beneficial drug to the environment of use according to claim 12, wherein the drug is released in a short period of time from the wall for providing beneficial drug instantly to the environment of use.

22. The osmotic device for the controlled delivery of a beneficial drug to the biological environment of use according to claim 12, wherein the drug in the wall is the same as the drug in the compartment.

23. The osmotic device for the controlled delivery of a beneficial drug to the biological environment of use according to claim 12, wherein the drug in the wall is different than the drug in the compartment.

24. The osmotic device for the controlled delivery of a beneficial drug to the biological environment of use according to claim 12, wherein the wall is formed in part of the semipermeable material with the remainder of the wall formed of an impermeable material.

25. The osmotic device for the controlled delivery of a beneficial drug to the biological environment of use according to claim 12, wherein the wall releases the drug in a pulsed therapeutically effective amount.

26. The osmotic device for the controlled delivery of a beneficial drug to the biological environment of use according to claim 12, wherein the device delivers drug from the compartment in a therapeutically effective amount over a prolonged period of time.

27. The osmotic device for the controlled delivery of a beneficial drug to the biological environment of use according to claim 12, wherein the shaped wall is a laminate comprising a semipermeable lamina and a microporous lamina.

28. The osmotic device for the controlled delivery of a beneficial drug to the biological environment of use according to claim 12, wherein the shaped wall comprises a lamina that contains the drug.

29. The osmotic device for delivering the beneficial agent according to claim 1, wherein the beneficial agent in the compartment is the same as the beneficial agent in the wall.

30. The osmotic device for delivering the beneficial agent according to claim 1, wherein the beneficial agent in the compartment is different than the beneficial agent in the wall.

31. The osmotic device for delivering the beneficial agent according to claim 1, wherein the beneficial agent formulation in the compartment exhibits an osmotic pressure gradient across the wall against a fluid present in the environment of use.

32. The osmotic device for delivering a beneficial drug to the environment of use according to claim 12, wherein the beneficial drug carried by the shaped wall is carried by a water soluble lamina.

33. The osmotic device for delivering a beneficial drug to the environment of use according to claim 12, wherein the shaped wall is a laminate and the beneficial drug is carried by a lamina coated onto the shaped wall.

34. The osmotic device for delivering a beneficial drug to the environment of use according to claim 12, wherein the shaped wall is a laminate comprising a semipermeable lamina and a microporous lamina, and the beneficial drug is carried by the microporous lamina.

* * * * *